(12) United States Patent
Hamachi et al.

(10) Patent No.: US 11,608,512 B2
(45) Date of Patent: Mar. 21, 2023

(54) METHOD FOR PRODUCING ORGANIC SUBSTANCE

(71) Applicant: SEKISUI CHEMICAL CO., LTD., Osaka (JP)

(72) Inventors: Kokoro Hamachi, Tsukuba (JP); Satoshi Shimizu, Tsukuba (JP)

(73) Assignee: SEKISUI CHEMICAL CO., LTD., Osaka (JP)

(*) Notice: Subject to any disclaimer, the term of this patent is extended or adjusted under 35 U.S.C. 154(b) by 0 days.

(21) Appl. No.: 17/275,369

(22) PCT Filed: Sep. 24, 2019

(86) PCT No.: PCT/JP2019/037341
§ 371 (c)(1),
(2) Date: Mar. 11, 2021

(87) PCT Pub. No.: WO2020/067050
PCT Pub. Date: Apr. 2, 2020

(65) Prior Publication Data
US 2022/0056486 A1 Feb. 24, 2022

(30) Foreign Application Priority Data

Sep. 25, 2018 (JP) .............................. JP2018-179526

(51) Int. Cl.
*C12N 1/02* (2006.01)
*C12P 7/08* (2006.01)
(Continued)

(52) U.S. Cl.
CPC ................ *C12P 7/08* (2013.01); *B01D 3/14* (2013.01); *B01D 5/0057* (2013.01); *C12N 1/02* (2013.01); *C12N 1/20* (2013.01)

(58) Field of Classification Search
None
See application file for complete search history.

(56) References Cited

U.S. PATENT DOCUMENTS

| | | | |
|---|---|---|---|
| 2013/0037402 A1* | 2/2013 | Pasanen | F26B 25/006 |
| | | | 202/159 |
| 2017/0260552 A1 | 9/2017 | Haas et al. | |
| 2022/0056486 A1* | 2/2022 | Hamachi | C12P 7/065 |

FOREIGN PATENT DOCUMENTS

| | | |
|---|---|---|
| JP | 2011-177159 A | 9/2011 |
| JP | 2016-029921 A | 3/2016 |

(Continued)

OTHER PUBLICATIONS

English Machine Translation of JP 2016-029921A, Abstract, Specification and Claims, Mar. 7, 2016 (Year: 2016).*

(Continued)

*Primary Examiner* — Richard C Ekstrom
(74) *Attorney, Agent, or Firm* — Sughrue Mion, PLLC

(57) ABSTRACT

Provided is a method which allows, for example, suppression of foaming in the purification step such as distillation and continuous operation, as well as direct treatment of a waste liquid (can liquid) without having to subject the same to an extra purification treatment by removing the microorganisms, nitrogen compounds, and phosphorous compounds at once from an organic substance-containing liquid obtained from microbial fermentation. Also disclosed is a method for producing an organic substance, comprising a microbial fermentation step, a separation step, a liquefaction step, and a second purification step, wherein the concentration of the nitrogen compound in the second can liquid is 0 to 150 ppm based on the total mass of the second can liquid, and the concentration of the phosphorous compound in the second can liquid is 0 to 5 ppm based on the total mass of the second can liquid.

7 Claims, 1 Drawing Sheet

(51) Int. Cl.
    *B01D 3/14*      (2006.01)
    *B01D 5/00*      (2006.01)
    *C12N 1/20*      (2006.01)

(56) References Cited

FOREIGN PATENT DOCUMENTS

| | | |
|---|---|---|
| JP | 2016-131549 A | 7/2016 |
| WO | 2011/064450 A1 | 6/2011 |
| WO | 2016/043163 A1 | 3/2016 |

OTHER PUBLICATIONS

Communication, dated Apr. 8, 2021, issued by the International Bureau in application No. PCT/JP2019/037341.
Office Action, dated Mar. 31, 2020, issued by the Japanese Patent Office in Japanese Patent Application No. 2019-555046.
Office Action, dated Jul. 28, 2020, issued by the Japanese Patent Office in Japanese Patent Application No. 2019-555046.
International Search Report for PCT/JP2019/037341, dated Dec. 24, 2019 [PCT/ISA/210].
Communication, dated May 30, 2022, issued by the European Patent Office in European Patent Application No. 19867754.4.

* cited by examiner

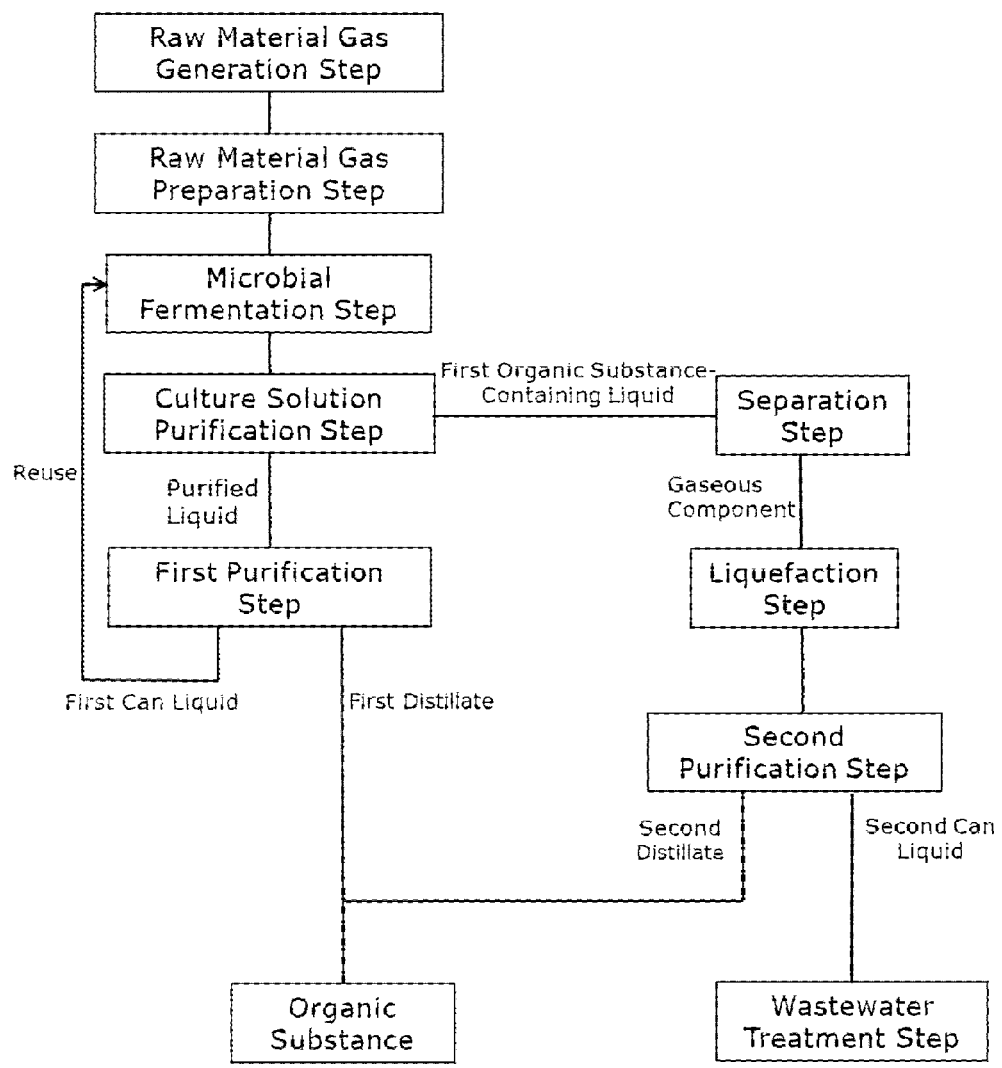

METHOD FOR PRODUCING ORGANIC SUBSTANCE

CROSS REFERENCE TO RELATED APPLICATIONS

This application is a National Stage of International Application No. PCT/JP2019/037341, filed Sep. 24, 2019, claiming priority based on Japanese Patent Application No. 2018-179526, filed Sep. 25, 2018.

BACKGROUND OF THE INVENTION

Field of the Invention

The present invention relates to a method for producing an organic substance and in particular, a method for producing an organic substance using an organic substance-containing liquid obtained by microbial fermentation.

Background Art

In recent years, methods for producing various organic substances from raw materials other than petroleum, for example, methods for producing bioethanol from edible raw materials such as corn by a sugar fermentation method have been of interest from the viewpoint of concerns about depletion of fossil fuel resources due to mass consumption of oils and alcohol produced from petroleum, and global environmental problems such as increase of carbon dioxide in the atmosphere. However, the sugar fermentation method using such edible raw materials has a problem of bringing about price escalation of food, for example, since the limited farmland area will be used for the production of products other than food.

In order to solve such problem, investigations are made to various methods for producing various organic substances which have been conventionally produced from petroleum, using non-edible raw materials which have been disposed. For example, there is known a method for producing ethanol by microbial fermentation from iron and steel exhaust gas, syngas obtained by gasification of waste, and the like.

In a method for producing ethanol from syngas by microbial fermentation, since ethanol produced by microbial fermentation is contained in the microbial fermentation vessel, there is a need to extract ethanol therefrom. As a method for extracting such ethanol, there is known a method using a distillation device.

As a method for producing an organic substance using microorganisms, there is known a method for isolating and purifying a desired organic substance. For example, Patent Document 1 proposes a method for removing a protein remaining in a lactic fermentation liquid, in which the protein is aggregated by heat denaturation and the aggregated substance is removed by solid-liquid separation.

PRIOR ART DOCUMENTS

Patent Document

Patent Document 1: JP2011-177159A

SUMMARY OF THE INVENTION

Problem to be Solved

The organic substance-containing liquid obtained by the above-described microbial fermentation contains a large amount of nitrogen compounds, phosphorous compounds, microorganisms, dead microorganisms, proteins derived from the microorganisms, and the like, apart from the desired organic substance. When the organic substance is extracted directly from such organic substance-containing liquid by, for example, a distillation device, etc., the microorganisms, etc. increase their concentration as the organic substance is distilled off, due to the effect by the microorganisms, etc. As a result, the viscosity of the organic substance-containing liquid in the distillation device increases to generate foaming in the distillation device, which can hinder continuous operation.

Further, even if the microorganisms were removed beforehand with the method disclosed in Citation 1 to extract the organic substance directly by for example, distillation, the nitrogen compounds and phosphorous compounds may remain in the waste liquid (can liquid). In such case, there is a need to further purify the waste liquid (can liquid), in order to meet the legal standard, for example, which as a result, increases the cost for manufacturing the organic substance.

It is therefore an object of the present invention to provide a method which allows, for example, suppression of foaming in the purification step such as distillation and continuous operation, as well as direct treatment of a waste liquid (can liquid) without having to subject the same to an extra purification treatment by removing the microorganisms, nitrogen compounds, and phosphorous compounds at once from an organic substance-containing liquid obtained from microbial fermentation.

Means for Solving the Problem

As a result of intensive studies to solve the problem as above, the present inventors have found that heating an organic substance-containing liquid obtained from microbial fermentation produces a solid or liquid component and a gaseous component, and by such separation thereof, the above-described object can be achieved, thereby completing the present invention. That is, the overview of the present invention is as follows.

[1] A method for producing an organic substance, comprising:

a microbial fermentation step of obtaining a first organic substance-containing liquid comprising an organic substance, a nitrogen compound, a phosphorous compound, and microorganisms by microbial fermentation;

a separation step of heating the first organic substance-containing liquid and separating into a liquid or solid component comprising the nitrogen compound, the phosphorous compound, and the microorganisms and a gaseous component comprising the organic substance;

a liquefaction step of liquefying the gaseous component comprising the organic substance by condensation to obtain a second organic substance-containing liquid comprising the organic substance, and a second purification step of separating a distillate comprising the organic substance and a second can liquid from the second organic substance-containing liquid, wherein the concentration of the nitrogen compound in the second can liquid is 0 to 150 ppm based on the total mass of the second can liquid, and the concentration of the phosphorous compound in the second can liquid is 0 to 5 ppm based on the total mass of the second can liquid.

[2] The method according to [1], further comprising a culture solution purification step of separating a purified liquid comprising the organic substance and a first organic substance-containing liquid comprising the organic substance, the nitrogen compound, the phosphorous compound, and the microorganisms from the first organic substance-containing liquid, after the microbial fermentation step.

[3] The method according to [2], further comprising a first purification step of separating a distillate comprising the organic substance and a first can liquid from the purified liquid.

[4] The method according to [3], comprising the step of reusing at least a portion of the first can liquid in the microbial fermentation and disposing at least a portion of the second can liquid.

[5] The method according to any one of [1] to [4], wherein the microbial fermentation uses a syngas comprising carbon monoxide as a raw material.

[6] The method according to [5], wherein the syngas is a waste-derived gas.

[7] The method according to any one of [1] to [6], wherein the organic substance comprises alcohol having 1 to 6 carbons.

Effect of the Invention

According to the present invention, it is possible to suppress foaming in the purification step such as distillation and carry out continuous operation, as well as carrying out direct treatment of a waste liquid (can liquid) without having to subject the same to an extra purification treatment by removing microorganisms, a nitrogen compound, and a phosphorous compound at once from an organic substance-containing liquid obtained from microbial fermentation.

BRIEF DESCRIPTION OF DRAWINGS

FIG. 1 is a figure of a process flow illustrating one example of the method for producing an organic substance according to the present invention.

EMBODIMENT OF THE INVENTION

Hereinafter, one example of preferred embodiments of the present invention will be described. However, the following embodiments are examples for illustrating the present invention, and the present invention is not limited in any way by the following embodiments. In the present specification, the proportion of each component in the gas is a proportion based on volume, not weight, unless otherwise specified. Thus, unless otherwise specified, percent by 100 represents percent by volume and ppm represents ppm by volume.

The method for producing an organic substance according to the present invention comprises a microbial fermentation step of obtaining a first organic substance-containing liquid comprising an organic substance, a nitrogen compound, a phosphorous compound, and microorganisms by microbial fermentation; a separation step of heating the first organic substance-containing liquid and separating into a liquid or solid component comprising the nitrogen compound, the phosphorous compound, and the microorganisms and a gaseous component comprising the organic substance; a liquefaction step of liquefying the gaseous component comprising the organic substance by condensation to obtain a second organic substance-containing liquid comprising the organic substance; and a second purification step of separating a distillate comprising the organic substance and a second can liquid from the second organic substance-containing liquid. In this case, the concentration of the nitrogen compound in the can liquid is 0 to 150 ppm based on the total mass of the entire can liquid, and the concentration of the phosphorous compound in the can liquid is 0 to 5 ppm based on the total mass of the entire can liquid. Note that, the method for producing the organic substance may further comprise a raw material gas generation step, a raw material gas purification step, a culture solution purification step, a first purification step, a waste water treatment step, and the like. FIG. 1 is a process flow indicating one example of the present invention. The process flow figure of FIG. 1 comprises a raw material gas generation step, a raw material gas purification step, a microbial fermentation step, a culture solution purification step, a first purification step, a separation step, a liquefaction step, a second purification step, and a waste water treatment step. Each step will be explained in the followings.

<Raw Material Gas Generation Step>

A raw material gas generation step is a step of generating a raw material gas by gasifying a carbon source (see FIG. 1). Note that, the raw material gas can be generated by reduction of carbon dioxide by reverse shift reaction.

There is no limitation to the raw material gas, and preferably, it contains carbon monoxide. Also, it may further contain components such as hydrogen, carbon dioxide, oxygen, nitrogen, tin, tar, nitrogen compound, sulfur compound, phosphorous compound, aromatic compound, and the like.

When the raw material gas contains carbon monoxide, the content of the carbon monoxide in the raw material gas is preferably, without particular limitation, 0.1 volume % or more, more preferably 10 volume % or more, further preferably 20 volume % or more, particularly preferably 20 volume % to 80 volume %, and most preferably 20 volume % to 60 volume %, with respect to the total volume of the raw material gas.

Note that a raw material gas containing carbon monoxide can generally be generated by conducting heat treatment (commonly known as gasification) in which a carbon source is combusted (incomplete combustion), i.e. by partially oxidizing the carbon source.

There is no particular limitation to the carbon source, and examples thereof include coal used in a coke oven, blast furnace (blast furnace gas), converter of a steel plant or a coal-fired power plant; waste introduced into an incinerator (especially gasification furnace) (non-industrial waste and industrial waste); biomass such as wood; and various carbon-containing materials for the purpose of recycling carbon dioxide, etc. which is subgenerated in various industries. Amongst these, the carbon source is preferably waste. In other words, the raw material gas is preferably a gas derived from waste.

Specifically, examples of the carbon source include plastic waste, garbage, municipal waste (MSW), waste tyres, biomass waste, domestic waste such as duvets and papers, waste such as building members, coal, petroleum oil, compounds derived from petroleum oil, natural gas, shale gas, and the like, and preferred amongst these is various waste, and more preferably non-segregated municipal waste from the view point of segregation costs.

Generation of the raw material gas is preferably carried out using a gasification furnace.

When a raw material gas containing carbon monoxide is generated, the gasification furnace which can be used is a furnace for combustion (incomplete combustion) of a carbon source. Specific examples include a shaft furnace, a kiln furnace, a fluidized bed furnace, and a gasification reforming furnace. The gasification furnace is preferably a fluidized bed furnace type because a high hearth load and excellent operability can be achieved by partially combusting the waste. The waste is gasified in a fluidized bed furnace at a low temperature (about 450 to 600° C.) and in a low oxygen atmosphere to be decomposed into char containing a large amount of gas (carbon monoxide, carbon dioxide, hydrogen, methane, etc.) and carbon. In addition, since the incombustibles contained in the waste are separated from the bottom of the furnace in a hygienic and lightly oxidized state, valuable substances such as iron and aluminum in the incombustibles can be selectively recovered. Therefore, gasification of such waste enables efficient recycling of resources.

The gasification temperature in the raw material gas generating step is usually 100° C. to 1500° C. and preferably 200° C. to 1200° C.

The reaction time for gasification in the raw material gas generating step is usually 2 seconds or more and preferably 5 seconds or more.

<Raw Material Gas Preparation Step>

The raw material gas as above may be supplied to the microbial fermenting vessel as a syngas as it is; however, the raw material gas may be purified so as to be suitable for the microbial fermentation.

When the raw material gas is derived from waste, the raw material gas tends to contain carbon monoxide in an amount of 0.1 vol % to 80 vol %, carbon dioxide in an amount of 0.1 vol % to 40 vol %, hydrogen in an amount of 0.1 vol % to 80 vol %, a nitrogen compound in an amount of 1 ppm or more, a sulfur compound in an amount of 1 ppm or more, a phosphorus compound in an amount of 0.1 ppm or more and/or an aromatic compound in an amount of 10 ppm or more. It may also contain substances such as other environmental contaminants, soot and dust particles, and impurities. Therefore, when the syngas is supplied to the microbial fermenting vessel, it is preferable to reduce or remove substances that are unfavourable for stable culturing of microorganisms and compounds, etc. in an undesired amount from the raw material gas so that the content of each component contained in the raw material gas is in a suitable range for stable culturing of microorganisms.

That is, the raw material gas purification step is a step of removing or reducing a specific substance such as various contaminants, soot and dust particles, impurities, and undesired amounts of compounds from the raw material gas (see FIG. 1). In the pretreatment step, syngas may be obtained from the raw material gas. The pretreatment step can be carried out using one or two or more of, for example, a gas chiller (a water separator), a low temperature (cryogenic) separation device, a cyclone, a particulate (soot) separator such as a bag filter, a scrubber (a water-soluble impurity separator), a desulfurizer (a sulfide separator), a membrane separator, a deoxygenator, a pressure swing adsorption separator (PSA), a temperature swing adsorption separator (TSA), a pressure temperature swing adsorption separator (PTSA), a separator using activated carbon, a separator using a copper or a palladium catalyst.

The raw material gas (hereinafter, the gas obtained by purifying the raw material gas may be referred to as "syngas") used in the method for producing an organic substance of the present invention preferably contains carbon monoxide. It may further contain hydrogen, carbon dioxide, and nitrogen.

The syngas used in the present invention may be a gas obtained by carrying out the steps of gasifying a carbon source to generate a raw material gas (a raw material gas generating step), and then adjusting the concentration of each component of carbon monoxide, carbon dioxide, hydrogen, and nitrogen and reducing or removing the above-mentioned substances and compounds from the raw material gas.

The concentration of carbon monoxide in the syngas is usually 20 volume % to 80 volume %, preferably 25 volume % to 50 volume %, and more preferably 35 volume % to 45 volume %, with respect to the total concentration of the carbon monoxide, carbon dioxide, hydrogen, and nitrogen in the syngas.

The concentration of hydrogen in the syngas is usually 10 volume % to 80 volume %, preferably 30 volume % to 55 volume %, and more preferably 40 volume % to 50 volume %, with respect to the total concentration of carbon monoxide, carbon dioxide, hydrogen, and nitrogen in the syngas.

The concentration of carbon dioxide in the syngas is usually 0.1 volume % to 40 volume %, preferably 0.3 volume % to 30 volume %, more preferably 0.5 volume % to 10 volume %, and particularly preferably 1 volume % to 6 volume %, with respect to the total concentration of carbon monoxide, carbon dioxide, hydrogen, and nitrogen in the syngas.

The concentration of nitrogen in the syngas is usually 40 volume % or less, preferably 1 volume % to 20 volume %, and more preferably 5 volume % to 15 volume % with respect to the total concentration of carbon monoxide, carbon dioxide, hydrogen, and nitrogen in the syngas.

The concentration of carbon monoxide, carbon dioxide, hydrogen, and nitrogen can be set to a predetermined range by changing the C—H—N element composition of the carbon source in the raw material gas generating step or by changing the combustion conditions such as the combustion temperature and the oxygen concentration of the supply gas during combustion, if necessary. For example, in the case where the concentration of carbon monoxide or hydrogen is to be changed, a carbon source having a high C—H ratio such as waste plastic may be used, and in the case where the concentration of nitrogen is to be lowered, gas having a high oxygen concentration may be supplied in the raw material gas generating step.

The syngas used in the present invention may, without particular limitation, contain a sulfur compound, a phosphorus compound, a nitrogen compound and the like in addition to the above components. The content of each of these compounds is preferably 0.05 ppm or more, more preferably 0.1 ppm or more, further preferably 0.5 ppm or more. The content of each compound is preferably 2000 ppm or less, more preferably 1000 ppm or less, further preferably 80 ppm or less, further more preferably 60 ppm or less, and particularly preferably 40 ppm or less. When the content of the sulfur compound, the phosphorus compound, the nitrogen compound, and the like is no less than the lower limit, there is an advantage that the microorganisms can be suitably cultured, and when the content is no more than the upper limit, there is an advantage that the culture medium is not contaminated by various nutrition sources which the microorganisms have not consumed.

Examples of the sulfur compound include sulfur dioxide, $CS_2$, COS, and $H_2S$, and preferred amongst them are $H_2S$ and sulfur dioxide as they are easily consumed as a nutrition source for the microorganisms. Therefore, it is more preferable that the syngas contains the sum of $H_2S$ and sulfur dioxide within the above ranges.

As the phosphorus compound, phosphoric acid is preferred as it is easily consumed as a nutrition source for the microorganisms. Therefore, it is more preferable that the syngas contains phosphoric acid within the above ranges.

Examples of the nitrogen compound include nitrogen monoxide, nitrogen dioxide, acrylonitrile, acetonitrile, HCN, and the like, and HCN is preferable in that it is easily consumed as a nutrient source for the microorganisms. Therefore, it is more preferable that the syngas contains HCN in the above range.

The syngas may contain an aromatic compound in the amount of preferably 0.01 ppm or more, more preferably 0.03 ppm or more, further preferably 0.05 ppm or more, and particularly preferably 0.1 ppm or more. The content of the aromatic compound is also preferably 90 ppm or less, more preferably 70 ppm or less, further preferably 50 ppm or less, and particularly preferably 30 ppm or less. The microorganisms tend to be cultured suitably by containing the aromatic compound in an amount no less than the lower limit. On the other hand, when the aromatic compound is contained in an amount no more than the upper limit, the culture medium tends to be less contaminated by various nutrition sources which the microorganisms have not consumed.

Note that, as mentioned above, the syngas is a purified gas of raw material gas, and preferably, the raw material gas is a gas derived from waste. Therefore, the syngas is preferably a gas derived from waste.

<Microbial Fermentation Step>

A microbial fermentation step is a step of obtaining a first organic substance-containing liquid comprising an organic substance, a nitrogen compound, a phosphorous compound, and microorganisms by microbial fermentation (see FIG. 1). In this case, normally a raw material gas obtainable from the raw material gas generation step or from a raw material gas (syngas) obtainable from the raw material gas purification step may be used in the microbial fermentation. Preferred amongst these is the use of the syngas in view of carrying out microbial fermentation in a suitable manner. Use may also be made to a syngas after adding another predetermined gas to the raw material gas obtainable from the raw material gas generation step or the raw material gas (syngas) obtainable from the raw material gas purification step. Examples of the other predetermined syngas include at least one compound selected from the group consisting of sulfuric compounds such as sulfur dioxide, phosphorus compounds, and nitrogen compounds. In one embodiment, the microbial fermentation preferably uses the raw material gas containing carbon monoxide or the syngas containing carbon monoxide as a raw material, and more preferably, the syngas containing carbon monoxide as a raw material. In this case, the raw material gas or the syngas is preferably a gas derived from waste. Herein under, the raw material gas or the syngas used in the microbial fermentation may be collectively referred to as "syngas, etc.".

Microbial fermentation is generally conducted in a microbial fermenting vessel. The microbial fermenting vessel used is preferably a continuous fermenter. In general, the microbial fermenting vessel may be of any shape, including a stirred type, an airlift type, a bubble column type, a loop type, an open-bond type, and a photobio type. Suitably used amongst these are known loop reactors having a main vessel part and a reflux part. When the loop reactors are used, a circulation step is preferably included, in which a liquid medium is circulated in between the main vessel part and the reflux part.

Although the syngas and the microbial culture solution may be continuously fed to the microbial fermenting vessel, the syngas and the microbial culture solution need not be fed simultaneously, and the syngas may be fed to the microbial fermenting vessel to which the microbial culture solution has been previously fed. It is known that some anaerobic microorganisms produce organic substances which are valuables such as ethanol, from a substrate gas such as a syngas by the fermenting action, and these gas-utilizing microorganisms are cultured in a liquid medium. For example, the liquid medium and the gas-utilizing bacteria may be fed and stored, and while the liquid medium is stirred in this state, the syngas may be fed into the microbial fermenting vessel. Accordingly, the gas-utilizing bacteria can be cultured in a liquid medium and by the fermenting action, an organic substance can be produced from the syngas.

As the temperature of the medium (culture temperature) in the microbial fermenting vessel, any temperature may be employed, and preferably can be about 30 to 45° C., more preferably about 33 to 42° C., and further preferably about 36.5 to 37.5° C.

The preferred culture time is 12 hours or longer with continuous culture, more preferably 7 days or longer, particularly preferably 30 days or longer, and most preferably 60 days or longer. Note that, the upper limit of the culture time is not determined; however, in view of periodic maintenance of the facility, the culture time is preferably 720 days or shorter and more preferably 365 days or shorter. Note that, the culture time is referred to as the time from adding the seed bacteria to the culturing vessel to the time when the entire amount of the culture solution in the culturing vessel is discharged.

The microorganisms (species) contained in the microbial culture solution are preferably those that can produce a desired organic substance by microbial fermentation of syngas using carbon monoxide as a main raw material (see FIG. 2). For example, the microorganisms (species) are preferably microorganisms which generate an organic substance from the syngas by the fermenting action of gas-utilizing bacteria, and particularly preferably microorganisms having a metabolic pathway of acetyl CoA. Among the gas-utilizing bacteria, the genus *Clostridium* is more preferred, and *Clostridium autoethanogenum* is particularly preferred, without particular limitation. The following is a further example.

Gas-utilizing bacteria include both eubacteria and archaebacteria. Examples of the eubacteria include *Clostridium, Moorella, Acetobacterium, Carboxydocella, Rhodopseudomonas, Eubacterium, Butyribacterium, Oligotropha, Bradyrhizobium*, and aerobic hydrogen-oxidizing bacteria, *Ralsotonia* bacteria, and the like.

On the other hand, examples of the archaebacteria include bacteria from the genus of *Methanobacterium, Methanobrevibacter, Methanocalculus, Methanococcus, Methanosarcina, Methanosphaera, Methanothermobacter, Methanothrix, Methanoculleus, Methanofollis, Methanogenium, Methanospirillium, Methanosaeta, Thermococcus, Thermofilum, Arcaheoglobus*, and the like. Amongst these, preferred as the archaebacterial are *Methanosarcina, Methanococcus, Methanothermobacter, Methanothrix, Thermococcus, Thermofilum*, and *Archaeoglobus*.

Further, preferred as the archaebacteria are bacteria from the genus of *Methanosarcina, Methanothermobactor*, or *Methanococcus*, and particularly preferred are *Methanosarcina* or *Methanococcus*, due to excellent carbon monoxide and carbon dioxide utilizing properties. Specific examples of the bacteria from the genus of *Methanosarcina* include *Methanosarcina barkeri, Methanosarcina mazei, Methanosarcina acetivorans*, and the like.

Among the above gas-utilizing bacteria, bacteria having a high ability to produce organic substances of interest are selected and used. For example, the gas-utilizing bacteria having a high ethanol-producing ability include *Clostridium*

*autoethanogenum, Clostridium* I *jungdahlii, Clostridium aceticum, Clostridium carboxidivorans, Moorella thermoacetica, Acetobacterium woodii*. Among these, *Clostridium autoethanogenum* is particularly preferable.

The medium used for culturing the above-described microorganisms (species) is not particularly limited, as long as it has an appropriate composition corresponding to the microorganisms, and is a liquid containing water as a main component and a nutrient (for example, vitamin, phosphoric acid, etc.) dissolved or dispersed in the water. The composition of such medium is prepared so that the gas-utilizing bacteria may grow well. For example, the medium in which the genus *Clostridium* is used as the microorganism can be prepared by using the specification of US2017/260552, paragraphs [0097] to [0099], etc. as a reference.

The first organic substance-containing liquid obtained from the microbial fermentation step includes the organic substance, a nitrogen compound, a phosphorous compound, and microorganisms, and other components.

Examples of the organic substance include, alcohols having 1 to 6 carbons, diols having 1 to 6 carbons, carboxylic acids having 1 to 6 carbons, hydroxycarboxylic acids having 1 to 6 carbons, ketones having 3 to 6 carbons, alkenes having 2 to 6 carbons, and alkadienes having 2 to 6 carbons.

Examples of the alcohols having 1 to 6 carbons include methanol, ethanol, propanol, isopropyl alcohol, and the like.

Examples of the diols having 1 to 6 carbons include 2,3-butanediol, and the like.

Examples of the carboxylic acids having 1 to 6 carbons include acetic acid, and the like.

Examples of the hydroxycarboxylic acids having 1 to 6 carbons include lactic acid, and the like.

Examples of the ketones having 3 to 6 carbons include acetone, and the like.

Examples of the alkenes having 2 to 6 carbons include isoprene, and the like.

Examples of the alkadienes having 2 to 6 carbons include butadiene, and the like.

Amongst these, preferably included as the organic substance are the alcohols having 1 to 6 carbons and the diols having 1 to 6 carbons, more preferably ethanol, propanol, isopropyl alcohol, and 2,3-butanediol, and further preferably ethanol. Note that, one of the organic substances as above may be contained alone, or 2 or more in combination.

Examples of the nitrogen compound include, without particular limitation, a component derived from a medium such as $NH_4Cl$ and $(NH_4)_2HPO_4$, a component derived from microorganisms such as a protein derived from microorganisms, and the like. Further, when the raw material gas (syngas) is a gas derived from waste, a component resulting from the raw material gas (syngas) may also be comprised.

Examples of the phosphorous compound include, without particular limitation, a component derived from a medium such as $H_3PO_4$ and $(NH_4)_2HPO_4$, a component derived from microorganisms such as nucleic acid, adenosine triphosphate (ATP), adenosine diphosphate (ADP), and the like. Further, when the raw material gas (syngas) is a gas derived from waste, a component resulting from the raw material gas (syngas) may also be comprised.

Examples of the microorganisms include microorganisms or the dead microorganisms.

Examples of the other components include water, medium components, and the like. Further, when the raw material gas (syngas) is a gas derived from waste, a component resulting from the raw material gas (syngas) may also be comprised.

Normally, the first organic substance-containing liquid is obtained as a suspension. In this case, although the concentration of the protein in the suspension varies depending on the kind of microorganisms, it is normally 30 to 1000 mg/L. Note that, the concentration of proteins in the first organic substance-containing liquid can be measured by Kjeldahl method.

<Culture Solution Purification Step>

A culture solution purification step is a step of separating a purified liquid comprising the organic substance and a first organic substance-containing liquid comprising the organic substance, the nitrogen compound, the phosphorous compound, and the microorganisms from the first organic substance-containing liquid after the microbial fermentation step. By including the culture solution purification step, the total amount of the first organic substance-containing liquid separated in the separation step to be described later will be reduced, and the separation step can be carried out efficiently and at a low cost.

Purification of the culture solution is done normally by a solid liquid separation such as a press machine, a centrifugation machine, and a filter. One of these methods may be used alone or two or more in combination.

The purified liquid from the culture solution purification comprises water and a water soluble component, other than the desired organic substance. In this case, examples of the water soluble component include nitrogen compounds such as $NH_4CL$ and phosphorous compounds such as $H_3PO_4$.

Although the first organic substance-containing liquid has a different composition from the first organic substance-containing liquid as of before the purification, it comprises the organic substance, the nitrogen compound, the phosphorous compound, the microorganisms, and the other components.

<First Purification Step>

A first purification step is a step of separating a distillate comprising the organic substance and a first can liquid from the purified liquid. This step is carried out when the above-described culture solution purification step is carried out. Since the purified liquid contains water, a water-soluble component, etc. other than the organic substance, it is possible to extract the organic substance by carrying out the first purification step. Note that, when a plurality of organic substances is generated by microbial fermentation, the purification condition, etc. is preferably adjusted by separating only the desired organic substance. When the condition was adjusted to separate only the desired organic substance, the distillate contains the desired organic substance and the can liquid contains the undesired organic substance.

Examples of the apparatus used in the first purification step include a distillation apparatus, a treatment apparatus including a pervaporation membrane, a treatment apparatus including a zeolite dehydration membrane, a treatment apparatus for removing a low boiling point substance having a boiling point lower than that of the organic substance, a treatment apparatus for removing a high boiling point substance having a boiling point higher than that of the organic substance, and a treatment apparatus including an ion exchange membrane. These apparatuses may be used alone or two or more in combination. As the unit operation, heat distillation or membrane separation may be suitably used.

Amongst these, the first purification step preferably includes heat distillation. That is, in one embodiment, the first purification step is a step of separating the distillate comprising the organic substance and the first can liquid from the purified liquid by thermal distillation.

The distillate comprises the organic substance. It can optionally comprise water, a water-soluble component, etc. Note that, when a plurality of organic substances is generated by microbial fermentation, the distillate comprises the desired organic substance and can optionally comprise water, a water-soluble component, an organic substance other than the desired organic substance, etc.

The first can liquid comprises water and a water soluble component. It can optionally comprise an organic substance. Examples of the water soluble component include nitrogen compounds such as $NH_4CL$ and phosphorous compounds such as $H_3PO_4$ as explained above. Note that, when a plurality of organic substances is generated by microbial fermentation, the distillate comprises an organic substance other than the desired organic substance, water, and a water-soluble component, and can optionally comprise the desired organic substance.

Note that, since the first can liquid may comprise a nitrogen compound and a phosphorous compound, there is a need for a further purification in order to meet the regulatory standard when the compounds are to be subjected to disposal treatment. Accordingly, at least a part, or preferably all of the first can liquid is reused for the microbial fermentation.

<Separation Step>

A separation step is a step in which the first organic substance-containing liquid is heated and separated into a liquid or solid component comprising a nitrogen compound, a phosphorous compound, and microorganisms, and a gaseous component comprising an organic substance. Note that, when the above-described culture solution purification step is conducted, the first organic substance-containing liquid obtained after the step is subjected to the purification step.

In conventional methods, when the first organic substance-containing liquid obtained from the microbial fermentation step is directly subjected to the purification step such as distillation as above to purify the organic substance, there was a problem that foaming is generated induced by the microorganisms, etc., interrupting the continuous operation.

There was also a problem that even when the microorganisms were removed beforehand and the organic substance was directly extracted by distillation for example, the nitrogen compound, the phosphorous compound, etc. may remain in the waste liquid (can liquid). In such case, the waste liquid (can liquid) must be purified further in order to, for example, meet the regulatory standard, which as a result, induces escalation of the manufacturing cost of the organic substance.

To such problem, the present invention utilizes the change in state by heating. That is, by heating the first organic substance-containing liquid, the organic substance is turned to gas and the nitrogen compound, the phosphorous compound, and the microorganisms are turned into liquid or solid, which makes it possible to separate only the desired organic substance. The separation step by heating makes it possible to remove the microorganisms and nitrogen and phosphorous compounds from the first organic substance-containing liquid at once. As a result, it is possible to suppress for example, foaming in the purification step such as distillation, in order to allow continuous operation, and also the waste liquid (can liquid) can be treated directly without having to subject the liquid to another purification treatment. Note that, the obtainable liquid or solid component is gasified again in the raw material gas generation step and used for producing ethanol or utilized for feeds (feeding stuffs) for livestock, fertilizers, solid fuels, materials for electrical generation or heat recovery, etc.

Examples of the liquid or solid component are a component that may turn into a liquid or solid state after heating the first organic substance-containing liquid. Specific examples include, a nitrogen compound, a phosphorous compound, microorganisms (including residues of the microorganisms), and other components, etc.

The gaseous component comprises the organic substance. The gaseous component may further comprise a component that turns into a gas state after heating the organic substance-containing liquid. Particular examples include water, in addition to organic substances.

Note that, when a plurality of organic substances is generated by microbial fermentation, the heating condition, etc. is preferably adjusted so that only the desired organic substance is separated. When the condition is adjusted to separate only the desired organic substance, the liquid or solid component comprises the undesired organic substance and the gaseous component comprises the desired organic substance.

In one embodiment, the desired organic substance is preferably ethanol, propanol, isopropyl alcohol, acetone, isoprene, and butadiene, more preferably ethanol, propanol, isopropyl alcohol, and acetone, further preferably ethanol and acetone, and particularly preferably ethanol.

The heating temperature of the organic substance-containing liquid varies depending on the kind of organic substances, and preferably is from 30 to 500° C., more preferably is from 50 to 200° C., further preferably is from 80 to 180° C., and particularly preferably is from 100 to 150° C.

The pressure at the time of heating is preferably 0.01 to 1000 kPa, more preferably 10 to 200 kPa, and further preferably 50 to 150 kPa.

In particular, the heating of the organic substance-containing liquid is preferably done at 50 to 200° C., more preferably at 80 to 180° C., and further preferably at 100 to 150° C., in view of economic efficiency, under normal pressure (101.3 kPa).

Note that, in one embodiment, the heating of the organic substance is at a temperature preferably 10 to 50° C. higher than the boiling point of the organic substance, more preferably 15 to 40° C. higher, and further preferably 20 to 30° C. higher. For example, in the case when ethanol (boiling point: 78° C.) is the desired organic substance, the organic substance-containing liquid is heated preferably at 88 to 128° C., more preferably at 93 to 118° C., and further preferably 98 to 108° C., under normal pressure.

The heating time in the separation step varies depending on the heating condition, and there is no particular limitation as long as the time is sufficient for obtaining the gaseous component. The heating time in the separation step is normally 5 seconds to 2 hours, preferably 5 seconds to 1 hour, and more preferably 5 seconds to 30 minutes, in view of efficiency and economic efficiency.

Note that, when a plurality of organic substances is to be generated by microbial fermentation, the heating condition, etc. is preferably adjusted so that only the desired organic substance is separated. For example, in the case when the desired organic substance is ethanol (boiling point: 78° C.) and when acetic acid (boiling point: 118° C.) is generated together with the ethanol, the desired organic substance, i.e. ethanol, can be turned in to the gaseous component and the acetic acid as the liquid component by determining the heating temperature to 100° C., so that only the desired organic substance, ethanol, can be purified. On the other hand, when the desired organic substances are both ethanol and acetic acid, then the desired organic substance, i.e.

ethanol and acetic acid can both be purified as a gaseous component from the solid component of microorganisms, etc.

Note that, as described above, when the desired organic substance has a boiling point (under normal pressure (101.3 kPa)) of 100° C. or less, the heating of the organic substance is preferably done to the temperature of 100° C. higher than the boiling point of the desired organic substance and the temperature of equal to or lower than 100° C., more preferably to the temperature of 15° C. higher and equal to or lower than 100° C., and further preferably to the temperature of 20° C. higher and equal to or lower than 100° C., under normal pressure. When the heating temperature is 10° C. higher than the boiling point of the desired organic substance, it is preferable since the desired organic substance can be suitably turned into gas. On the other hand, it is preferable when the heating temperature is no higher than 100° C., since the heating can be achieved by heating of the water which may be contained in the organic substance-containing liquid, which is easily achieved and cost reducing.

The device used in the above-described separation step is not particularly limited, as long as it can efficiently separate the organic substance-containing liquid into a liquid or a solid component (microorganisms, dead microorganisms, proteins derived from the microorganisms, etc.) and a gaseous component (the organic substance) by heat energy. Examples of specific devices include drying devices such as a rotary dryer, a fluidized bed dryer, a vacuum type dryer, and a conduction heating type dryer. Among these, from the viewpoint of efficiency in separating the liquid or solid component and the gaseous component from the organic substance-containing liquid particularly having a low solid component concentration, it is preferable to use a conduction heating type dryer. Examples of the conduction heating type dryer include a drum type dryer and a disk type dryer.

<Liquefaction Step>

The liquefaction step is a step of liquefying the gaseous component comprising the organic substance by condensation to obtain a second organic substance-containing liquid comprising the organic substance (see FIG. 1).

The device used in the liquefaction step is preferably, without particular limitation, a heat exchanger, particularly a condenser. Examples of the condenser include a water-cooled condenser, an air-cooled condenser, and an evaporation condenser. Among them, the water-cooled type is preferable. The condenser may be of a single stage or multiple stages.

The second organic substance-containing liquid comprises an organic substance. It may also comprise water, etc.

Although it is deemed preferable that the second organic substance-containing liquid obtained by the liquefaction step is free of the components comprised in the first organic substance-containing liquid such as a nitrogen compound, a phosphorous compound, microorganisms, and the like, the present invention does not exclude the presence of the nitrogen compound, the phosphorous compound, microorganisms, and the like in the second organic substance-containing liquid.

Condensation heat of the gaseous component obtained by a condenser can be used as a heat source in the purification step as described later. By reusing the condensation heat, the organic substance can be produced efficiently and economically.

<Second Purification Step>

A second purification step is a step of separating a distillate comprising the organic substance and a second can liquid from the second organic substance-containing liquid (see FIG. 1).

Examples of the apparatus used in the second purification step include a distillation apparatus, a treatment apparatus including a pervaporation membrane, a treatment apparatus including a zeolite dehydration membrane, a treatment apparatus for removing a low boiling point substance having a boiling point lower than that of the organic substance, a treatment apparatus for removing a high boiling point substance having a boiling point higher than that of the organic substance, and a treatment apparatus including an ion exchange membrane. These apparatuses may be used alone or two or more in combination. Suitable use made for the unit operation is heat distillation or membrane separation.

Among these, the second purification step preferably includes heat distillation. That is, in one embodiment, the second purification step is preferably a step of separating the distillate comprising the organic substance and the second can liquid from the second organic substance-containing liquid by heat distillation.

In the thermal distillation, a desired organic substance can be obtained as a distillate with high purity using a distillation apparatus. The temperature in the distillation apparatus at the time of distillation of the organic substance (particularly ethanol) is not particularly limited, and is preferably 110° C. or less, more preferably 100° C. or less and further preferably about 70 to 95° C. Setting the temperature in the distillation apparatus within the above range will ensure necessary separation of the organic substance from the other components, i.e., distillation of the organic substance.

The pressure in the distillation apparatus during distillation of the organic substance may be a normal pressure; however, preferred pressure is less than normal pressure and more preferred is about 60 to 95 kPa (absolute pressure). Setting the pressure in the distillation apparatus within the above range allows improvement of the separation efficiency of the organic substance, which can lead to improvement in the yield of the organic substance. Although depending on the kind of the desired organic substance, the yield when, for example the organic substance is ethanol, (concentration of ethanol contained in the distillate after distillation) is preferably 90% by weight or more and more preferably 95% by weight or more.

In the membrane separation, a known separation membrane can be used appropriately, for example, a zeolite membrane can be used appropriately.

The concentration of the organic substance comprised in the second distillate separated in the second purification step is preferably 20 to 99.99% by mass and more preferably 60 to 99.9% by mass.

On the other hand, the concentration of the organic substance comprised in the second can liquid is preferably 0.001 to 10% by mass and more preferably 0.01 to 5% by mass.

In the manufacturing method according to the present invention, the can liquid separated in the purification step contains the nitrogen compound and the phosphorous compound each in a concentration reduced to 0 to 150 ppm and 0 to 5 ppm as described above. In the preferred embodiment of the present invention, the can liquid is substantially free of the nitrogen compound and the phosphorous compound. In the present invention, "substantially free" does not mean that the concentration of the nitrogen compound is 0 ppm, but means that the concentration of the nitrogen compound and the phosphorous compound in the can liquid obtained in the purification step is in a level that requires no waste water treatment step that would satisfy the environmental standard designated by law. In the separation step, the first organic substance-containing liquid is separated into a liquid or solid component comprising a nitrogen compound, a phosphorous compound, and microorganisms, and a gaseous component comprising an organic substance as described above, and the desired organic substance is not purified from the first organic substance-containing liquid obtained in the microbial fermentation step. In this case, since the nitrogen and phosphorous compounds and microorganisms remain in the liquid or solid component side, the gaseous component comprising the organic substance contains almost no nitrogen compound or phosphorous compound. Therefore, it is considered that the nitrogen and phosphorous compounds are substantially not contained in the can liquid obtained when the organic substance is purified from the liquefied product obtained by liquefying the gaseous component. Even when the can liquid contains a nitrogen compound, the concentration of the nitrogen compound is 0.1 to 150 ppm, preferably 0.1 to 120 ppm. Further, even in the case in which the can liquid comprises a phosphorous compound, the concentration of the phosphorous compound is preferably 0.1 to 5 ppm and more preferably 0.1 to 1 ppm. Note that, each concentration of the nitrogen compound and the phosphorous compound in the can liquid can be measured using a known analyzing instrument such as a inductively-coupled plasma emission spectrometer (ICP-AES) and the like.

Note that, the can liquid separated from the second organic substance-containing liquid normally comprises water. In the case where a plurality of the organic substance is generated by microbial fermentation, the can liquid may comprise other organic substances than the desired organic substance.

Further, the can liquid separated from the purified liquid normally contains water, a nitrogen compound, and a phosphorous compound. In the case where a plurality of the organic substance is generated by microbial fermentation, the can liquid may comprise other organic substances than the desired organic substance.

In this manner, the can liquid discharged in the purification step of the organic substance is substantially free of the nitrogen or the phosphorus compound according to the present invention, and since it is considered that there is hardly any other organic substances contained, the waste water treatment step conventionally required can be simplified, and as a result, the energy cost required for disposal can be reduced.

<Wastewater Treatment Step>

The second can liquid separated in the second purification step may be subjected to a waste water treatment step (see FIG. 1). In the waste water treatment step, organic substances such as nitrogen compounds and phosphorus compounds can be further removed from the second can liquid. In this step, the organic substance may be removed by subjecting the second can liquid to anaerobic treatment or aerobic treatment. The removed organic substance may be used as a fuel (heat source) in the purification process.

The treatment temperature in the waste water treatment step is usually 0 to 90° C., preferably 20 to 40° C., and more preferably 30 to 40° C.

Since the liquid or solid component comprising the nitrogen and phosphorous compounds and microorganisms and the like are removed from the second can liquid obtained through the separation step as above, the load of waste water treatment, etc. is reduced compared with the can liquid obtained by directly supplying the purification step from the microbial fermentation step.

In the waste water treatment step, the concentration of the nitrogen compound in the treated liquid obtained by treating the second can liquid is 0 to 150 ppm, preferably 0.1 to 100 ppm, more preferably 0.1 to 50 ppm, and further preferably 0.1 to 10 ppm, and particularly preferably, no nitrogen compound is contained. The concentration of the phosphorus compound in the treatment liquid is 0 to 50 ppm, preferably 0.1 to 10 ppm, more preferably 0.1 to 5 ppm, and further preferably 0.1 to 1 ppm, and particularly preferably, no phosphorus compound is contained in the can liquid.

One Preferred Embodiment

According to one preferred embodiment, the method for producing an organic substance comprises a microbial fermentation step of obtaining a first organic substance-containing liquid comprising an organic substance, a nitrogen compound, a phosphorous compound, and microorganisms by microbial fermentation; a culture solution purification step of separating a purified liquid comprising the organic substance and the first organic substance-containing liquid comprising the organic substance, the nitrogen compound, the phosphorous compound, and the microorganisms from the first organic substance-containing liquid, after the microbial fermentation step; a first purification step of separating a distillate comprising the organic substance and a first can liquid from the purified liquid; a separation step of heating the first organic substance-containing liquid and separating into a liquid or solid component comprising the nitrogen compound, the phosphorous compound, and the microorganisms and a gaseous component comprising the organic substance; a liquefaction step of liquefying the gaseous component comprising the organic substance by condensation to obtain a second organic-substance containing liquid comprising the organic substance; and a second purification step of separating a distillate comprising the organic substance and a second can liquid from the second organic substance-containing liquid. In this case, the concentration of the nitrogen compound in the second can liquid is 0 to 150 ppm based on the total mass of the second can liquid, and the concentration of the phosphorous compound in the second can liquid is 0 to 5 ppm based on the total mass of the second can liquid. Additionally, at least a part of the first can liquid is reused for the microbial fermentation, and at least a part of the second can liquid is disposed.

According to the preferred embodiment above, since the culture solution purification step is present in the first place, the total amount of the first organic substance-containing liquid can be reduced, which is to be subjected to the separation step. As a result, it is possible to achieve the separation efficiency and to reduce the manufacturing cost. Additionally, by reusing at least a part or preferably the total amount of the first can liquid obtained through separation of the purified liquid by the culture solution purification step, the first purification step, for microbial fermentation, the cost for discharging the can liquid can be reduced. Further, the presence of both the first and the second purification steps makes it possible to obtain the first can liquid which may contain the nitrogen and phosphorous compounds and the second can liquid which contains no or hardly any nitrogen or phosphorous compounds separately. As a result, it is possible to divide so that the first can liquid is reused and the second can liquid is disposed, and also by using both, the impurities can be prevented or suppressed from being concentrated which is accompanied by continuous culturing.

<Organic Substance and Use Thereof>

Examples of the organic substance obtainable from the manufacturing method according to the present invention include methanol, ethanol, 2,3-butanediol, acetic acid, lactic acid, isoprene, butadiene, and the like, and preferably comprises alcohols or diols having 1 to 6 carbons, more preferably alcohols or diols having 1 to 4 carbons, and further preferably ethanol. The use purpose of the organic substance obtainable from the manufacturing method according to the present invention is not particularly limited. The produced organic substance can be used as a raw material for, for example, plastics, resins, and the like, and can also be used as various solvents, fungicides, or fuels. The high-concentration ethanol can be used as fuel ethanol mixed with gasoline, etc., and can also be used as an additive for cosmetics, beverages, chemical substances, raw materials of fuels (jet fuel), food, etc., having extremely high versatility.

EXAMPLES

The present invention will be described in more details with reference to Examples; however, the present invention is not limited to the following Examples to the extent the scope of the invention is not exceeded.

Example 1

A continuous fermenter (fermenting vessel) provided with a main reactor, a syngas supply hole, a medium supply hole, and a discharge hole was filled with bacteria of genus *Clostridium* and a liquid culture medium (containing an appropriate amount of a phosphorus compound, a nitrogen compound, various minerals, and the like) for culturing the bacteria.

Next, a syngas composed of 30 volume % of carbon monoxide, 10 volume % of carbon dioxide, 35 volume % of hydrogen and 25 volume % of nitrogen was prepared, fed into the continuous fermenter, and culture (microbial fermentation) was carried out at 37° C.

After the culture, the organic substance-containing liquid discharged from the microbial fermenting vessel was collected. The obtained organic substance-containing liquid was a suspension containing ethanol, microorganisms, dead microorganisms, and the like, and when the concentration of the nitrogen compound and the phosphorous compound in the organic substance-containing liquid was measured using ICP-AES, the values were 425 mg/L and 191 mg/L, respectively. The concentration of the proteins was 170 mg/L. Note that, the concentration of the proteins was measured in accordance with Kjeldahl method.

The organic substance-containing liquid obtained by culture was heated by a conduction heating type drying device (CD dryer, SCD-500, manufactured by Nishimura Works Co., Ltd.) at 120 to 125° C. under normal pressure, and the organic substance-containing liquid was separated into a liquid or solid component and a gaseous component. The separated gaseous component was condensed by a condenser and liquefied to obtain a liquefied product. The concentration of the nitrogen compound and the phosphorous compound in the obtained liquefied product was measured to be 119 ppm and 0.05 ppm, respectively. Note that, the protein concentration was determined to be 13 mg/L.

Next, assuming the distillation process is to be carried out in the distillation column, a foaming test was conducted by bubbling while the obtained liquefied product was heated, and almost no foaming was confirmed.

Comparative Example 1

A foaming test by bubbling was also conducted on the organic substance-containing liquid used in Example 1, and vigorous foaming was confirmed.

From the above results, it has become clear that the liquefied product obtained by heating an organic substance-containing liquid comprising microorganisms, separating the liquid or solid component comprising microorganisms, etc. and the gaseous component containing the organic substance, and condensing the gaseous component can suppress foaming in the subsequent purification process.

The invention claimed is:

1. A method for producing an organic substance, comprising:
    a microbial fermentation step of obtaining a first organic substance-containing liquid comprising an organic substance, a nitrogen compound, a phosphorous compound, and microorganisms by microbial fermentation;
    a separation step of heating the first organic substance-containing liquid which is a suspension by using a conduction heating type dryer and separating into a liquid or solid component comprising the nitrogen compound, the phosphorous compound, and the microorganisms and a gaseous component comprising the organic substance;
    a liquefaction step of liquefying the gaseous component comprising the organic substance by condensation to obtain a second organic substance-containing liquid comprising the organic substance, and
    a second purification step of separating a distillate comprising the organic substance and a second can liquid from the second organic substance-containing liquid, wherein
    the concentration of the nitrogen compound in the second can liquid is 0 to 150 ppm based on the total mass of the second can liquid, and the concentration of the phosphorous compound in the second can liquid is 0 to 5 ppm based on the total mass of the second can liquid.

2. The method according to claim 1, further comprising a culture solution purification step of separating a purified liquid comprising the organic substance and a first organic substance-containing liquid comprising the organic substance, the nitrogen compound, the phosphorous compound, and the microorganisms from the first organic substance-containing liquid, after the microbial fermentation step.

3. The method according to claim 2, further comprising a first purification step of separating a distillate comprising the organic substance and a first can liquid from the purified liquid.

4. The method according to claim 3, comprising the step of reusing at least a portion of the first can liquid in the microbial fermentation and disposing at least a portion of the second can liquid.

5. The method according to claim 1, wherein
    the microbial fermentation uses a syngas comprising carbon monoxide as a raw material.

6. The method according to claim 5, wherein
    the syngas is a waste-derived gas.

7. The method according to claim 1, wherein
    the organic substance comprises alcohol having 1 to 6 carbons.

* * * * *